(12) United States Patent
Arata (10) Patent No.: US 6,890,953 B2
(45) Date of Patent: May 10, 2005

(54) PROCESS FOR TREATING WATER (75) Inventor: Andrew B. Arata, Lake City, FL (US)

(73) Assignee: Innovative Medical Services, El Cajon, CA (US)

(*) Notice: Subject to any disclaimer, the term of this patent is extended or adjusted under 35 U.S.C. 154(b) by 0 days.

(21) Appl. No.: 10/103,548

(22) Filed: Mar. 20, 2002

(65) Prior Publication Data

US 2003/0178374 A1 Sep. 25, 2003

Related U.S. Application Data (63) Continuation-in-part of application No. 09/544,404, filed on Apr. 6, 2000, now abandoned.

(51) Int. Cl.$^7$ .................. A01N 55/02; A01N 59/16; A61L 2/18; C02F 1/467; C02F 1/50
(52) U.S. Cl. .................. 514/495; 514/574; 514/970; 424/618; 424/DIG. 6; 422/22; 422/28; 205/440; 205/457; 210/748; 210/749; 210/764
(58) Field of Search ................. 514/495, 574, 514/970; 424/618, DIG. 6, 619; 422/22, 28; 205/440, 457; 210/748, 749, 764

(56) References Cited

U.S. PATENT DOCUMENTS

| | | | |
|---|---|---|---|
| 3,422,183 A | 1/1969 | Ellison | |
| 3,702,298 A | 11/1972 | Zsoldos | |
| 4,021,578 A | 5/1977 | Harich et al. | |
| 4,180,473 A | 12/1979 | Maurer et al. | |
| 4,264,592 A | 4/1981 | Xhajanka | |
| 4,291,125 A | 9/1981 | Greatbatch | |
| 4,297,374 A | 10/1981 | Wess | |
| 4,385,632 A | 5/1983 | Odelhog | |
| 4,564,461 A | 1/1986 | Skold et al. | |
| 4,608,183 A | 8/1986 | Rossmoore | |
| 4,666,616 A | 5/1987 | Rossmoore | |
| 4,708,808 A | 11/1987 | Rossmoore | |
| 4,755,268 A | 7/1988 | Matsuo et al. | |
| 4,780,216 A | 10/1988 | Wojtowicz | |
| 4,889,844 A | 12/1989 | Silvetti, Sr. et al. | |
| 4,915,955 A | 4/1990 | Gomori | |
| 4,933,178 A | 6/1990 | Capelli | |
| 5,017,295 A | 5/1991 | Antelman | |
| 5,063,062 A | 11/1991 | Greenspan et al. | |
| 5,073,382 A | 12/1991 | Antelman | |
| 5,078,902 A | 1/1992 | Antelman | |
| 5,089,275 A | 2/1992 | Antelman | |
| 5,177,065 A | 1/1993 | Silvetti, Sr. et al. | |
| 5,332,511 A | 7/1994 | Gay et al. | |
| 5,362,714 A | 11/1994 | Radford et al. | |
| 5,364,649 A | 11/1994 | Rossmoore et al. | |
| 5,373,025 A | 12/1994 | Gay | |
| 5,382,337 A | 1/1995 | Wlassics et al. | |
| 5,464,559 A | 11/1995 | Marchin et al. | |
| 5,503,840 A | 4/1996 | Jacobson et al. | |
| 5,510,109 A | 4/1996 | Tomioka et al. | |
| 5,660,840 A | 8/1997 | Pruett | |
| 5,962,517 A | 10/1999 | Murad | |
| 6,017,461 A | 1/2000 | Garvey et al. | |
| 6,139,823 A | 10/2000 | Drechsler et al. | |
| 6,181,963 B1 | 1/2001 | Chin et al. | |
| 6,197,814 B1 | 3/2001 | Arata | |

FOREIGN PATENT DOCUMENTS

WO    WO 00/27390    * 5/2000

OTHER PUBLICATIONS

Chemical Abstracts. 87:74283n Complexes of Silver(I) with some hydroxy acids. Tsimbler, S. M.; Novikova, L. S. (USSR). Zh. Neorg. Khim. 1977, 22(7) 1842–6 (Russ).

Chemical Abstracts. 69:8964n Preservatives for Tobacco. Paul Richii. Swiss 446991 (CL. A 24b), Mar. 15, 1968, Appl. Apr. 22, 1964; 2pp.

* cited by examiner

*Primary Examiner*—John Pak
(74) *Attorney, Agent, or Firm*—McDermott Will & Emery LLP (57) ABSTRACT

A process is disclosed for treating impure water by introducing a solution of electrolyticially generated silver citrate into the impure water wherein the silver is electrolytically generated in a solution of citric acid and water.

10 Claims, 4 Drawing Sheets

PROCESS FOR TREATING WATER

CROSS-REFERENCE TO RELATED APPLICATIONS

This application is a continuation-in-part of Ser. No. 09/544,404, filed Apr. 6, 2000, now abandoned.

BACKGROUND OF THE INVENTION

1. Field of the Invention

This invention relates to water treatment and more particularly to an improved disinfectant for use in treating impure water.

2. Description of the Related Art

The prior art has demonstrated that the presence of copper and silver ions in an aqueous solution is useful as a disinfectant. Many in the prior art have used copper and silver ions in an aqueous solution as a disinfectant in water systems such as cooling towers, swimming pools, hot water systems in hospitals, potable water systems, spa pools and the like.

Typically, copper and silver electrodes were connected to a direct current power supply. When the direct current was applied to the copper and silver electrodes, copper and silver ions were generated by an electrolysis process from the copper and silver ions within the water. In one example of the prior art, water was passed continuously through an ion chamber having copper and silver electrodes. The water emanating from the ion chamber contained the copper and silver ions generated by copper and silver electrodes within the ion chamber. The water emanating from the ion chamber containing the copper and silver ions was used as a disinfectant in water systems such as cooling towers, swimming pools, hot water systems in hospitals, potable water systems, spa pools and the like. The copper and silver ions within the water systems acted as a disinfectant for controlling algae, viruses, bacteria and the like.

U.S. Pat. No. 3,422,183 to Ellison discloses biocide compositions comprising ultra-violet irradiated silver fluoride solutions containing colloidal silver resulting from the irradiation and kept in dispersion by a protective colloid, e.g., casein or gelatin, and biocide uses thereof in sline control, against pathogens or other microbes in food or beverage containers or processing equipment, as an ingredient of wood preservatives, as a bactericide in paints, as a biocide in synthetic polymer films, as a sterilant in bandages, and biocide-like uses in other areas.

U.S. Pat. No. 3,702,298 to Zsoldos discloses a method of maintaining a highly oxidizing aqueous solution intended primarily for treatment of swimming pool water. A metal having a multiple valence is interacted to a lower valence with oxidizable debris in the solution, and the metal is continuously re-oxidized to a higher valence by maintaining in the water a constant excess of an oxidizer bank consisting of a salt of a peroxy acid. Silver, copper and nickel are suitable metals and their salts have germicidal properties which are greatly increased and the spectrum broadened by converting the mono salt to a divalent or trivalent salt.

U.S. Pat. No. 4,180,473 to Maurer et al. discloses a method of transporting metal ions by introducing a metal complex into a medium containing a moiety which demands the metal ion and the complex releases the ions in a controlled manner upon demand. The metal complexes have an aqueous proton induced dissociation property represented by a sigmoidally-shaped curve on a cartesian coordinate plot of the negative log of the metal ion concentration versus the negative log of hydrogen ion concentration. This dissociation property causes a controlled release of metal ion into mediums containing a reacting moiety upon demand for the metal ion. For example, metal working emulsions of oil and water are stabilized by the addition thereto of minor amounts of a metal complex, e.g. disodium monocopper (II) citrate, which at alkaline pH metalworking conditions above about 7 to about 9 releases metal catons to the emulsions imparting stabilizing characteristics which prevent emulsion degradation by a number of factors commonly encountered in metalworking operations. Also, the method is effective in the controlled release of metal ions in the normal range of physiological pH, i.e. about 4 to 9, for growth controlling action against microorganisms including bacteria, fungi and viruses.

U.S. Pat. No. 4,291,125 to Greatbatch discloses a method and apparatus for killing plant and animal bacteria and plant viroids by electrically generated silver ions. The silver ions serve as germicidal agents in infection control and are generated by very slow electrical anodic corrosion of a silver wire located closely adjacent the infection site. In particular, a silver anode and a cathode of non-corroding metal are located in an electrolytic nutrient medium with the silver anode being within five millimeters of the infection site, and a direct voltage is applied to the anode and cathode in a manner passing a positive current in the microampere range into the silver anode causing it to corrode slightly and give off silver ions which produce a germicidal environment about the infection site.

U.S. Pat. No. 4,385,632 to Odelhog discloses an absorbent body for collecting blood, feces and urine containing a water-soluble copper salt which impedes bacterial growth, prevents the breaking-down of urea into ammonia and complex-binds ammonia so as to prevent the occurrence of unpleasant odor. Preferably copper acetate is used, in which even the acetate ion has germicidal effect.

U.S. Pat. No. 4,564,461 to Skold et al. discloses mechanical working of cast iron performed in the presence of an aqueous metal working composition containing an organic copper (II) complex and an iron corrosion inhibitor. An aqueous concentrate, which after dilution with water is suitable for application in mechanical working of cast iron, contains 1–50% copper (II) complex with such a $Cu_2+$ content of 0.5–20%, 1–50% iron corrosion inhibitor, 0–50% lubricant, 0–20% pH-regulators, bactericides and solubilizing agents and 10–70% water.

U.S. Pat. No. 4,608,183 to Rossmoore discloses antimicrobial mixtures of isothiazolones and a metal complex with a polyfunctional ligand which are synergistic. The mixtures particularly include mixtures of a monocopper disodium citrate as the ligand and a 5-x-2-lower alkyl 4-isothiazolin-3-one wherein x is a halo or hydrogen group as the isothiazolone. The compositions are particularly useful for metal cutting fluids wherein long duration antimicrobial activity is desired.

U.S. Pat. No. 4,666,616 to Rossmoore discloses synergistic anti-microbial compositions containing a mixture of a metal complex of a polyfunctional organic liquid and a biocidal composition which contains or releases a lower aldehyde containing 1 to 5 carbon atoms. The compositions are particularly useful as metal working fluids at alkaline pH and have a broad spectrum of activity against fungi and bacterial.

U.S. Pat. No. 4,708,808 to Rossmoore discloses synergistic anti-mircrobial compositions containing a mixture of a metal complex of a polyfunctional organic ligand and a biocidal composition which contains or releases a lower aldehyde containing 1 to 5 carbon atoms. The compositions are particularly useful as metal working fluids at alkaline pH and have a broad spectrum of activity against fungi and bacteria.

U.S. Pat. No. 4,780,216 to Wojtowicz discloses a sanitizing composition consisting essentially of a mixture of a calcium hypochlorite compound and a peroxydisulfate compound having the formula: $M_xS_2O_8$ where M is an alkali metal or alkaline earth metal, and x is 1 or 2 is employed in treating water to improve pH control and provide increased removal of organic materials. The compositions provide improved sanitation of water in swimming pools, spas, and cooling towers by efficiently oxidizing organic impurities while helping to minimize the increase in the pH of the water. This permits a reduction in the amount and frequency of addition of acidic compounds such as hydrochloric acid to the water bodies. Further, the incorporation of additives such as algaecides, dispersant, and clarifying agents provides for significant improvements in water quality as evidenced by sparkling pure water.

U.S. Pat. No. 4,915,955 to Gomori discloses a concentrate with an unlimited shelf-life, which can be mixed with hydrogen peroxide at a ratio of 1:99 to 1:199 to become an effective disinfectant, is obtained when a viscous solution of inorganic acid, with a pH less than or equal to 1.6, is mixed with a silver salt compound or a colloidal silver compound at 50 to 66 C. The mixture is further combined at room temperature with other inorganic acid(s) to reach a total of 100 g inorganic acid(s) per liter of water at room temperature, an organic acid stabilizer is added and the mixture is homogenized. The concentrate, during storage, remains homogeneous and crystal-clear.

U.S. Pat. No. 4,933,178 to Capelli discloses a medical device with an antimicrobial coating that is safe, effective, photostable and readily manufacturable produced by applying a composition to at least one body fluid-contacting surface of the device such that a solid coating is provided on that surface, the coating composition comprising an oligodynamic metal salt of a sulfonylurea, a polymeric material, at least one acid compound selected from the group consisting of a water-soluble carboxylic acid and water-insoluble carboxylic acid, and a carrier liquid in which foregoing components are soluble. The antimicrobial coating accommodates variation in the release of antimicrobial metal ions as a function of the intended use for a medical device to which the coating is applied.

U.S. Pat. No. 5,017,295 to Antelman discloses a method or methods of controlling the growth of bacteria in the water of swimming pools and/or industrial water supplies by adding to the water a specified concentration of a stable divalent silver compound. The invention has the advantage over chlorination in that it is odorless and non-volatile. It furthermore is superior to monovalent silver compounds as these compounds do not decompose in the presence of light and resist precipitation by halides and form divalent soluble complexes which in the monovalent state are invariably insoluble solids.

U.S. Pat. No. 5,073,382 to Antelman discloses a solid alkaline bactericidal compositions suitable for compounding alkaline end products such as food and dairy cleaners and surgical scrubbing soaps, formed by the neutralization of acid stabilized inorganic divalent silver complexes and capable of effecting 100% kills upon cultures of anaerobic bacteria colonies of 100 K/cc. within 5 minutes.

U.S. Pat. No. 5,078,902 to Antelman discloses divalent silver halides providing a source for divalent bactericidal silver ions in the presence of persulfate. The halides are especially effective when applied to water used in industrial cooling installations, hot tubs and swimming pools and will conform to stringent EPA requirements for waters utilized for bathing as in tubs and pools of 100% kills of 100 K/cc E. Coli coliforms within 10 minutes, exemplary of which are the chloride and bromide which give 100% kills within 5 minutes. The halides, of course, can be used in salty water since they are solids immune from halide action that would otherwise precipitate soluble divalent silver from solution.

U.S. Pat. No. 5,089,275 discloses solid bactericidal compositions based on divalent silver (Ag(II)) as the active sanitized agent. The compositions are prepared by reacting acid liquid Ag(II) complexes with anhydrous calcium sulfate so as to form a solid matrix in which the bactericide is entrapped in the resulting hydrated calcium sulfate. Optimum compositions are described consisting of Ag(II) of solid (by weight) to liquid (by volume) is 5:2. The resulting solid bactericides can be used in water cooling installations. They are capable of causing 100% kills within 10 minutes of E. Coli conforms in conformity with EPA protocols, allowing them to qualify as swimming pool and hot tub sanitizers. Since the compositions are based on calcium sulfate, they are also suitable as mineralizers, thus providing a dual function.

U.S. Pat. No. 5,332,511 to Gay et al. discloses a process for sanitizing water in swimming pools, spas and hot tubs whereby the level of bacteria in said water is lowered comprising treating said water with a bactericidal effective amount of a combination of diisodecyl dimethyl ammonium chloride and copper (II) ions, the concentration of diisodecyl dimethyl ammonium chloride in said water being less than about 60 parts per million parts of water by weight and treating said water at least intermittently with an oxidant selected from the group consisting of available chlorine and ozone.

U.S. Pat. No. 5,364,649 to Rossmoore et al. discloses activity of antimicrobial compounds selected from isothiazolones and compounds which release formaldehyde enhanced with a metal complex of a lower alkanolamine, particularly copper (cupric) trietha-iolamine. The enhancement is particularly useful in metalworking fluids.

U.S. Pat. No. 5,373,025 to Gay discloses a sanitizer composition comprising a bactericidal effective amount of the combination of (a) a quaternary ammonium compound selected from the group consisting of (hydrogenated tallow) 2-ethylhexyl dimethyl ammonium salt, dicoco dimethyl ammonium salt, and mixtures thereof; and (b) a copper (II) ion source.

U.S. Pat. No. 5,382,337 to Wlassics et al. discloses a process for oxidizing organic materials or compounds in aqueous phase, with hydrogen peroxide and in the presence of ferrous ions FE-(II), and optionally cupric ions cu-(II), carried out under irradiation with artificial visible light.

U.S. Pat. No. 5,464,559 to Marchin et al. discloses a composition provided for treating drinking water for disinfecting and/or removing iodide. The composition utilizes resin bound silver ions. For performing the disinfection or iodide removal with minimal release of silver ions into the water being treated, a chelating resin having iminodiacetate chelating groups is employed, and the resin is loaded with not over 0.5 mole of silver ions per mole of iminodiacetate.

U.S. Pat. No. 5,503,840 to Jacobson et al. discloses an antimicrobial composition of titanium dioxide, barium sulfate, zinc oxide particles, and mixtures thereof having successive coatings of silver, in some cases a coating of zinc and/or copper compounds such as zinc oxide, copper (II) oxide and zinc silicate; silicon dioxide; alumina; and a dispersion aid such as dioctyl azelate.

U.S. Pat. No. 5,510,109 to Tomioka et al discloses an antibacterial and antifungal composition which comprises an antibacterial and antifungal material carried on a porous particle carrier. Preferably, the porous particle carrier is a silica gel particle. The antibacterial and antifungal material is at least one metal complex salt, and can contain plant extracts and the like in addition to the metal complex salt. At least a portion of the surface of the above-mentioned carrier having the antibacterial and antifungal composition can be coated with a coating material.

U.S. Pat. No. 6,017,461 to Garvey et al. discloses a water purification systems including a tank fed from a main water supply and an electrolytic ion generator including silver alloy electrodes. A pump circulates water from the tank through the ion generator and back into the tank at a rate of at least 1 L/s to gradually ionize the contents of the tank and generate a concentrate of silver-ion-laden water. An injector feeds the concentrate into the water system as required.

Unfortunately, these copper and silver ions within an aqueous solution have only a limited stable ionic life. After a limited time, the copper and silver ions form complexes with other elements thus diminishing the concentration of the copper and silver ions within the aqueous solution. Accordingly, the aqueous solution had to be replenished with copper and silver ions to maintain the concentration of the copper and silver ions within the aqueous solution. The aqueous solution may be replenished with copper and silver ions by constantly circulating the aqueous solution thorough the ion chamber.

In my prior U.S. Pat. No. 6,197,814, I disclosed a novel aqueous disinfectant comprising an aqueous solution of silver citrate wherein the silver is electrolytically generated in a solution of citric acid and water. It is that object to the present invention to utilize the novel aqueous disinfectant to of my prior U.S. Pat. No. 6,197,814 for the treatment all of impure water.

Therefore, it is an object of the present invention to provide a process for treating impure water by introducing a solution of electrolyticially generated silver citrate into the impure water wherein the silver is electrolytically generated in a solution of citric acid and water.

Another object of this invention is to provide a process for treating impure water that is will reduce coliform bacteria to internationally recognized standards.

Another object of this invention is to provide a process for treating impure water that is effective in production potable water.

Another object of this invention is to provide a process for treating impure water that is an effective control against rectal and total coliform bacteria.

Another object of this invention is to provide a process for treating impure water that is free from halogen components.

Another object of this invention is to provide a process for treating impure water that is non-toxic and environmentally friendly.

Another object of this invention is to provide a process for treating impure water in either a batch process or a continuous process.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

A specific embodiment of the present invention is described and shown in the attached Detailed Description. For the purpose of summarizing the invention, the invention relates to a process for treating impure water. The process comprises forming a solution of electrolyticially generated silver citrate by electrolyticially generating silver ions within a solution of citric acid and water. The solution of electrolyticially generated silver citrate is introduced into the impure water.

In a more specific example of the invention, the step of forming the solution of electrolyticially generated silver citrate includes forming the solution of electrolyticially generated silver citrate to have a concentration between of 500 and 10,000 parts per million in water. In one example of the invention, the electrolytically generated silver citrate has a concentration between of 2000 parts per million in water.

In another more specific example of the invention, the step of introducing the solution of electrolyticially generated silver citrate includes introducing the solution of electrolyticially generated silver citrate at a concentration of 100 parts per billion of impure water.

The step of introducing the solution of electrolyticially generated silver citrate into the impure water may include continuously metering the solution of electrolyticially generated silver citrate into moving impure water. In the alternative, the step of introducing the solution of electrolyticially generated silver citrate into the impure water may include injecting the solution of electrolyticially generated silver citrate into a batch of impure water.

The foregoing has outlined rather broadly the more pertinent and important features of the present invention in order that the detailed description that follows may be better understood so that the present contribution to the art can be more fully appreciated. Additional features of the invention will be described hereinafter which form the subject of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which.

Similar reference characters refer to similar parts throughout the several Figures of the drawings.

DETAILED DISCUSSION

Figure 1:
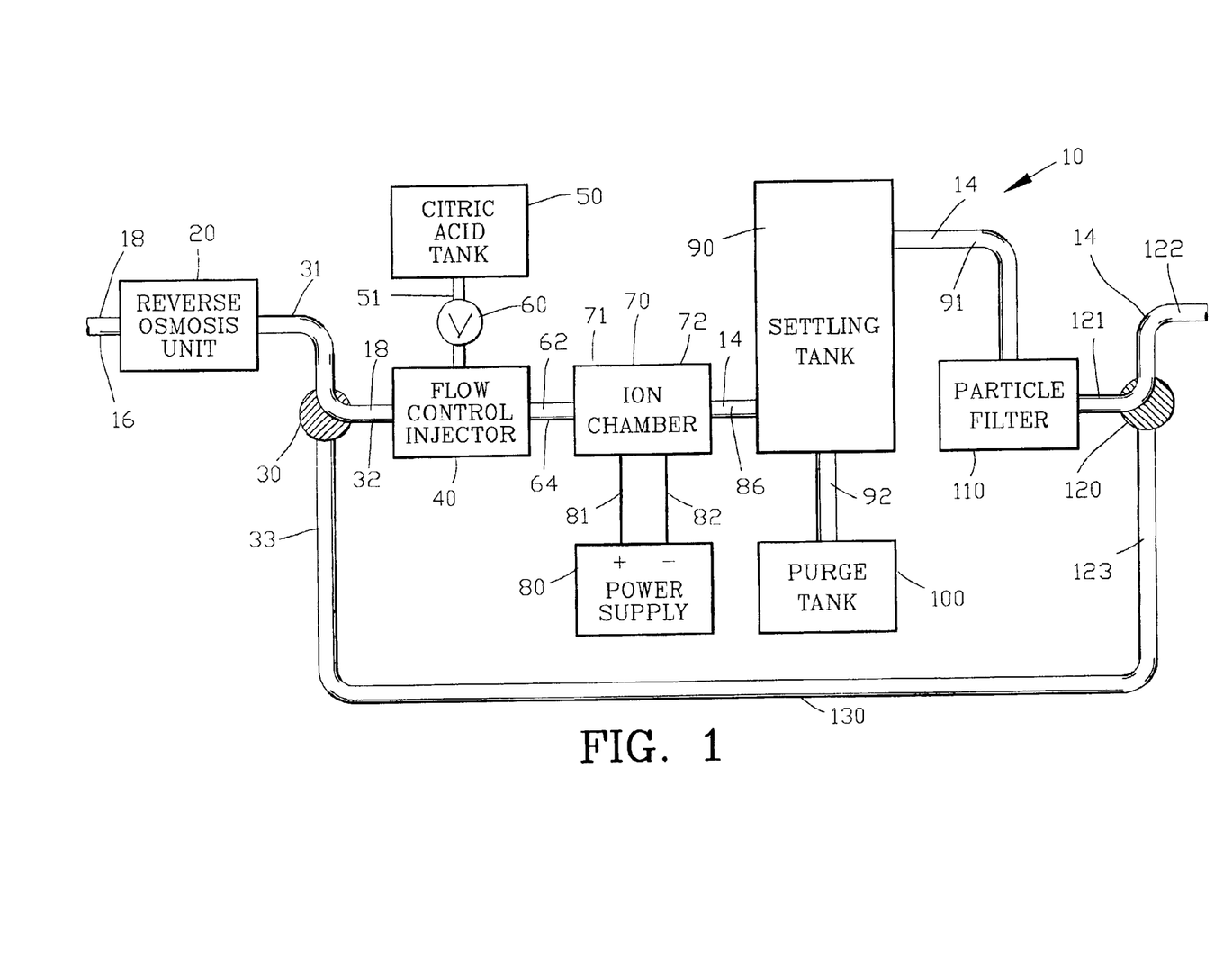
FIG. 1 is a diagram of a first process of making the disinfectant of the present invention.

FIG. 1 is a diagram of a first process 10 of making the disinfectant 14 of the present invention. The first process 10 is shown as a continuous process of making the disinfectant 14. It should be understood that the first process 10 of FIG. 1 is only an example of a process and numerous other variations and/or processes may be utilized to make the disinfectant 14 of the present invention.

The disinfectant 14 may be used immediately for any suitable application such as a disinfectant in a water system including cooling towers, hot water systems, potable water systems, or any other suitable application or surface.

The first process 10 comprises a water input conduit 16 for introducing water 18 from a water source (not shown) to a water treatment unit shown as a reverse osmosis unit 20. The reverse osmosis unit 20 passes the water 18 from the water input conduit 16 through a semi-permeable membrane (not shown) for removing impurities from the water. Although the water treatment unit is shown as a reverse osmosis unit 20 it should be understood that various water treatment units may be employed within the process shown in FIG. 1. Preferably, the water 18 emanating from the reverse osmosis unit 20 is deionized medically pure water.

The water 18 emanating from the reverse osmosis unit 20 is directed to a valve 30 through a conduit 31. The valve 30 directs the water 18 though a conduit 32 to a flow control injector 40. A citric acid tank 50 contains concentrated citric acid. The concentrated citric acid is directed by a conduit 51 to a metering valve 60 for metering the concentrated citric acid into the flow control injector 40. The flow control injector 40 mixes the concentrated citric acid with the water 18 to provide a dilute citric acid solution 62. The metering valve 60 controls the concentration of the citric acid within the water 18. The diluted citric acid solution 62 is directed by a conduit 62 into an ion chamber 70.

Figure 3:
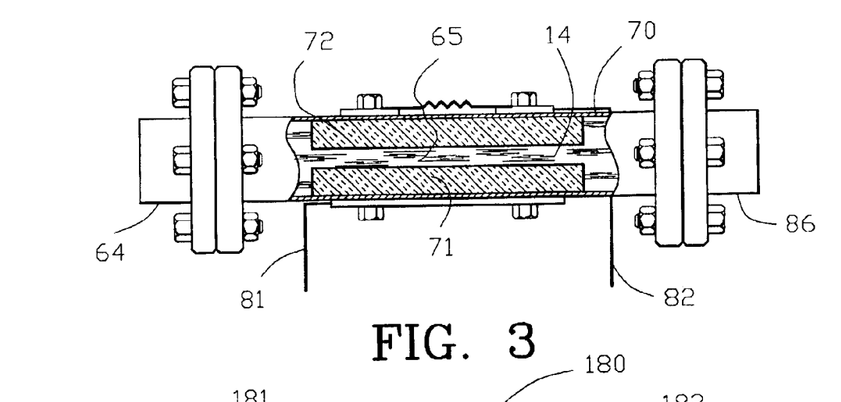
FIG. 3 is an enlarged detailed view of the ion chamber of FIGS. 1 and 2.

FIG. 3 is an enlarged detailed view of the ion chamber 70 of FIG. 1. The ion chamber 70 includes a positive and a negative electrode 71 any 72. The positive and negative electrodes 71 and 72 are located in a spaced apart position for enabling the diluted citric acid solution 62 to pass between the positive and negative electrodes 71 and 72. Each of the positive and negative electrodes 71 and 72 is fabricated from elemental silver. Preferably, the positive and negative electrodes 71 and 72 are formed from 99.9999% pure elemental silver.

A direct current power supply 80 includes a positive and a negative conductor 81 and 82 connected to the positive and negative electrodes 71 and 72. The positive and negative electrodes 71 and 72 are spaced apart a suitable distance such as 2.0 to 8.0 centimeters to allow an ionic current flow between the positive and negative electrodes 71 and 72.

Upon energizing the direct current power supply 80, an ion current flows between the positive and negative electrodes 71 and 72. The direct ion current flow between the positive and negative electrodes 71 and 72 produces electrolytically free silver ions within the diluted citric acid solution 62. The silver ions react with the citric acid in the diluted citric acid solution 62 to produce the disinfectant 14 of the present invention.

The disinfectant 14 is directed by a conduit 86 to a settling tank 90. The settling tank 90 includes an overflow conduit 91 and a drain conduit 92. The disinfectant 14 exits the settling tank 90 through the overflow conduit 91. Any precipitated materials from the disinfectant 14 within the settling tank 90 fall to the bottom of the settling tank 90. The precipitated materials at the bottom of the settling tank 90 may be removed through the drain conduit 92 to a purge tank 100. The precipitated materials in the purge tank 100 may be recycled.

The disinfectant 14 exiting through the overflow conduit 91 from the settling tank 90 is directed to a particle filter 110. Although the particle filter 110 may be any suitable filter, preferably the particle filter 110 is a submicron filter. The filtered disinfectant 14 is directed to a valve 120 by a conduit 121. The valve 120 directs the filtered disinfectant 14 to a conduit 122 for discharge from the first process 10.

The filtered disinfectant 14 discharged from conduit 122 may be used immediately for any suitable application such as a disinfectant in a water system or any other suitable application. In the event a greater concentration of the disinfectant 14 is desired, the disinfectant 14 may be recirculated for increasing the concentration of the disinfectant 14.

Figure 2:
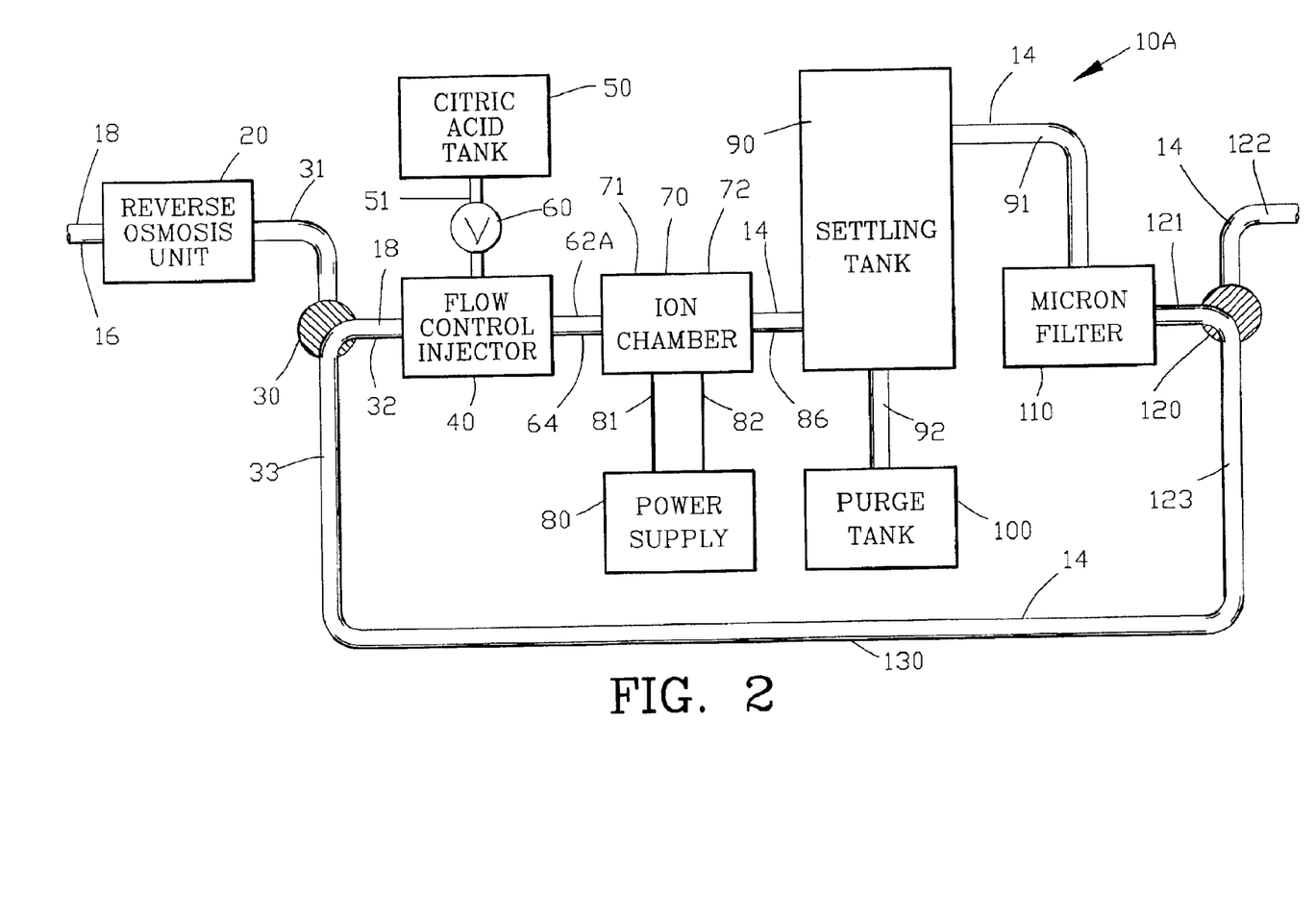
FIG. 2 is a diagram of a second process of making the disinfectant of the present invention.

FIG. 2 is a diagram of a second process 10A of making the disinfectant 14 of the present in a concentrated form. The second process 10A is shown as a recirculating process of making the disinfectant 14 and for increasing the concentration of the disinfectant 14. In the concentrated form, the disinfectant 14 may be bottled for use at a later time. It should be understood that the second process 10A of FIG. 2 is only an example of a process and numerous other variations and/or processes may be utilized to make the disinfectant 14 of the present invention.

In the second process 10A shown in FIG. 2, the valve 30 and 120 are move into positions opposite to the positions shown in FIG. 1. The valve 120 directs the filtered disinfectant 14 to a conduit 123. The conduit 123 is connected through a conduit 130 to the conduit 32 of the valve 30.

The valve 30 directs the filtered disinfectant 14 though the conduit 32 to the flow control injector 40. Additional concentrated citric acid is directed through the metering valve 60 into the flow control injector 40. The flow control injector 40 mixes the concentrated citric acid with the filtered disinfectant 14 to increase the concentration of the citric acid solution 62A.

The citric acid solution 62A is directed into an ion chamber 70 to produce additional silver ions within the citric acid solution 62A. The silver ions react with the citric acid in the citric acid solution 62A to increase the concentration of the disinfectant 14. The disinfectant 14 is passed through the settling tank 90 to exit through the overflow conduit 91. The disinfectant 14 is filtered by the particle filter 110 and is directed to the valve 120 by the conduit 121.

The valve 30 and 120 are maintained in positions shown in FIG. 2 to continue to recirculate the disinfectant 14 for increasing the concentration of the disinfectant 14. Upon obtaining the desired concentration of the disinfectant 14, the valve 120 may be moved to the position shown in FIG. 1 to discharge the disinfectant 14 from the conduit 122.

Figure 4:
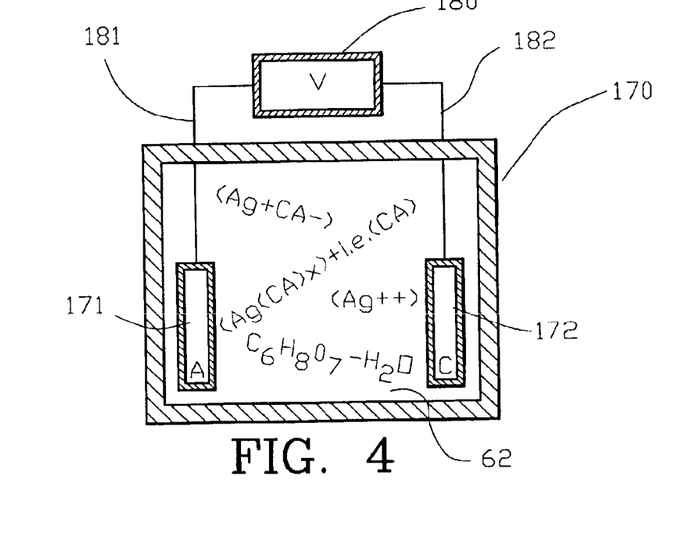
FIG. 4 is an enlarged detailed view of an ion chamber suitable for making the disinfectant of the present invention in a batch process.

FIG. 4 is an enlarged detailed view of an ion chamber 170 suitable for making the disinfectant of the present invention in a batch process. The ion chamber 170 includes a positive and a negative electrode 171 and 172. Each of the positive and negative electrodes 171 and 172 is fabricated from 99.9999% pure elemental silver.

The positive and negative electrodes 171 and 172 are located in a spaced apart position for enabling the citric acid solution 162 to pass between the positive and negative electrodes 171 and 172. Preferably, the positive silver electrode 171 is spaced relative to a negative electrode 172 a distance sufficient to enable silver ion flow therebetween. The spacing of the positive and negative electrodes 171 and 172 has been shown in an exaggerated fashion in FIG. 4. Preferably, a spacing of approximately 2.0 to 8.0 mm. has been found to be suitable for the above concentration of citric acid and water.

A direct current power supply 180 includes a positive and a negative conductor 181 and 182 connected to the positive and negative electrodes 171 and 172. Upon energizing the direct current power supply 180, an ion current flows between the positive and negative electrodes 171 and 172. The direct ion current flow between the positive and negative electrodes 171 and 172 produces electrolytically free silver ions within the citric acid solution 162. The silver ions react with the citric acid in the citric acid solution 162 to produce the disinfectant 14 of the present invention.

The process of making a disinfectant comprises electrolytically generating silver ions in a solution of citric acid and water to form an aqueous solution of silver citrate. Preferably, the solution of citric acid and water comprises a solution of approximately 5.0% to 10% citric acid in water by volume. A potential difference of 12 volts to 50 volts provides a flow of silver ions in the range of 0.1 amperes to 0.5 amperes per square inch. A more fuller explanation of the content of the solution within the ion chamber 170 will be described in greater detail hereinafter.

The prior art has established in that the generation of both silver ions and copper ion in water provides the best disinfectant properties. The combination of silver ions and copper ions provides superior disinfecting properties than either silver ions alone or copper ions alone. This synergistic effect of silver ions and copper ions in water has been well established by the prior art.

In contrast to this established prior art, the disinfectant of the present invention is formed in a solution of citric acid and water rather than water alone. Additionally, the disinfectant of the present invention has superior properties with only silver ions alone rather than the combination of both silver ions and copper ions. The silver ions of the present process react with the citric acid to form a silver citrate. The silver citrate provides superior disinfectant properties over the prior art process of generating silver and copper ions in water.

In further contrast to the established prior art, the disinfectant of the present invention has a stable ionic form having an extended useful shelf-life. The useable shelf-life of the disinfectant of the present invention enables the aqueous disinfectant solution to be packaged in an aqueous concentrate form.

The improved disinfectant is an aqueous solution of silver citrate wherein the silver is electrolytically generated in a solution of citric acid and water. The silver citrate formed in accordance with the above process has different characteristics than other forms of silver citrate.

Concentrations of 0.1% silver citrate by volume have been formulated in accordance with the above process. A concentration of 0.1% silver citrate by volume corresponds to 1000 parts per million (ppm). The concentration of 0.1% silver citrate was formed in a solution of citric acid and water comprises approximately 10.0% citric acid by volume. Higher concentration of the silver citrate are believed to be obtainable by the above process. It appears the higher the concentration of citric acid in water, the higher the concentration of silver citrate formed by the above process.

The Merck Index, Eleventh Edition (1989) page 1348 states that silver citrate is soluble in 3500 parts water. A concentration of 1 to 3500 corresponds to 285 parts per million (ppm). Obviously, the silver citrate formed in accordance with the above process has different solubility than other forms of silver citrate.

Nuclear magnetic resonance tests (1H NMR) were preformed on the silver citrate formed in accordance with the above process and a blank citric acid sample. The samples showed an overwhelming excess of citric acid, with little or no other anions present. It is postulated the Ag must be in the form of the cation $Ag^+$ complexed with the citric acid. It is theorized the empty $5s$ orbital of Ag+ overlaps with the delocalized $\delta$ bond on one of the carboxyl groups of citric acid. The citric acid anion is the counterion for this complex ion $(Ag(CA)_x^+ (Cit)^-)$. Cit is citric acid or is $(C_6H_7O_7-H_2O)$. Another possibility is a zwitterion, where the negative charge is on the complex itself, $(Ag^+Cit^-)$, wherein $Cit^-$ is $(C_6H_7O_7)^-$ where the total charge of the complex is neutral. Either or both of these species may exist in the silver citrate formed in accordance with the above process. Multiple complexation to $Ag^+$ is also possible.

Further speculation based on test data from several types of spectroscopy including UV/Visible absorption and fluorescence spectroscopy, infrared spectroscopy, NMR spectroscopy, and mass spectroscopy indicate that the predominant silver-containing species is a salt containing one silver ion per citrate ion. This salt is not a colloid and may not be a complex (i.e., an entity containing one or a few silver ions bound to several citrate ions). The chemical formula of the salt may be $AgC_6H_7O_7$, and may be named silver dihydrogen citrate.

The electrolytically generated silver citrate appears to be different from non-electrolytically generated silver citrate $(Ag_3C_6H_5O_7)$, which is the standard silver citrate salt described in the literature and which contains three silver ions per citrate ion. The solubility of the electrolytically generated silver citrate $AgC_6H_7O_7$ in water appears to be higher than the non-electrolytically generated silver citrate $(Ag_3C_6H_5O_7)$. The solubility of the electrolytically generated silver citrate $AgC_6H_7O_7$ in water is 2410 parts per million (PPM) whereas the solubility of the non-electrolytically generated silver citrate $(Ag_3C_6H_5O_7)$ in water is 280 parts per million (PPM).

Figure 5:
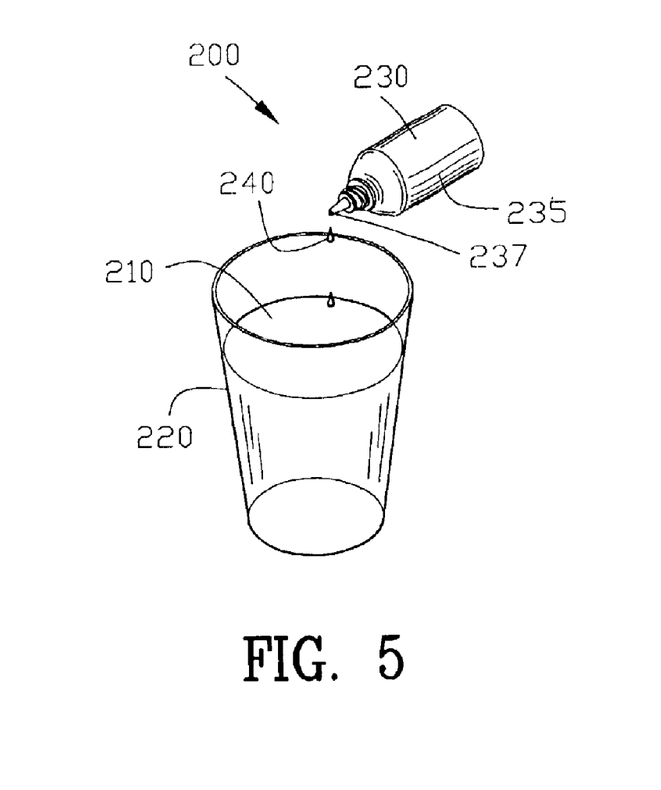
FIG. 5 is an isometric view of a process of treating a batch of impure water.

FIG. 5 is an isometric view of a process 200 of treating a batch of impure water 210. In this example of the indenture on impure water 210 is retained within a container 220 shown as a drinking glass. The disinfectant 14A comprises a treating solution 230 of the electrolyticially generated silver citrate formed by electrolytically generating silver ions within a solution of citric acid and water as described heretofore. The treating solution 230 is contained in a solution container 235 having a dropper opening 237.

The treating solution 230 has a concentration between of 500 and 10,000 parts per million in water with a preferred concentration of 2000 parts per million in water. The treating solution 230 comprises approximately 5.0% to 20.0% citric acid by volume and approximately 0.05% to 1.0% by volume of silver citrate formed by the electrolytically generated silver.

FIG. 5 illustrates the process step of introducing treating solution 230 into the batch of impure water 210. In this example, the treating solution 230 is introduced manually into the batch of impure water 210 by the drop 240 from the dropper opening 237 of the solution container 235. The following is an example the process of treating a batch of impure water 210 wherein the treating solution 220 has a concentration of 2000 ppm and the treating solution 220 is induced into the impure water 210 at concentration of 100 parts per billion of impure water 210.

EXAMPLE 1

Procedure In Case of Natural Disasters

In case of emergency, follow the instructions that are detailed below: If the water that is going to be purified comes from a river or other source that is highly contaminated (dark color), take a piece of fabric to filter the water of solids and fill a one liter bottle with the water already filtered. Add 10 drops of the treating solution 210, and wait for 10 minutes. Although it doesn't look very clean, this water is purified. Drink the water after the 10 minutes. If the water looks clean because it comes from the pipe or a river or other source, you don't need to filter the water. Add 5 drops of the treating solution 210, wait 10 minutes and drink it. Follow the same procedure in case that you are going to use the water to wash fruits, meat, vegetables and/or any food. The water treated with treating solution 210, can be given to the babies, sick people or pregnant women. Follow the above instructions and will avoid any kind of health problems or epidemics that are usual in the natural disasters.

Figure 6:
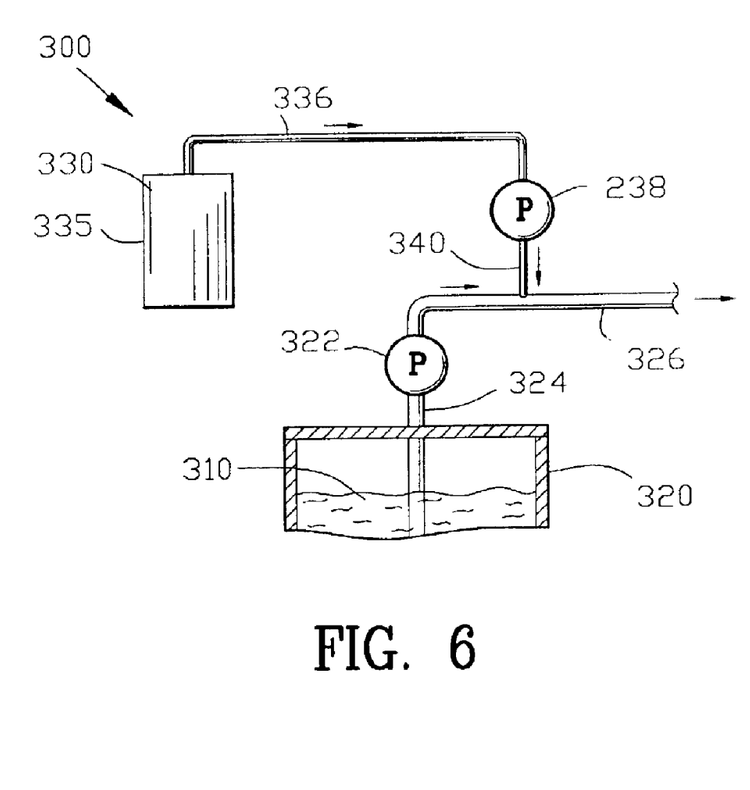
FIG. 6 is a diagram of a process of continuously treating impure water.

FIG. 6 is a diagram of a process 300 of continuously treating impure water 310. In this example the invention, impure water 310 is located within a water source 310 shown as a well 320. Although the water source 310 has been shown as a well, it should be appreciated by those killed in the art that the water source 310 may be other water sources such as a reservoir or the like. A pump 320 withdraws the impure water 310 from the water source 310 through a conduit 324 for discharge from a conduit 326.

The treating solution 330 is introduced continuously from a solution container 335. A metering pump 338 withdraws the treating solution 330 from the solution container 335 through a conduit 336 for discharge from a conduit 340. The pumping speed of the pump 320 and the metering pump 338 are established to provide the proper introduction of the treating solution 320 within the impure water 310. Preferably, at concentration of treating solution 320 has a concentration of 2000 ppm and the treating solution 320 is induced into the impure water 310 at concentration of 100 parts per billion of impure water 310.

Table 1 illustrates the efficacy of the treating solution 210. The tests, conducted using a 30-ppm strength use dilution treating solution 210 formula, were designed to demonstrate the kill activity of the treating solution 210 on hard surfaces. The tests were performed by nationally recognized independent laboratories under Association of Analytical Chemists (AOAC) protocol and Good Laboratory Practices in accordance with EPA regulations. At 30 part per million (ppm) concentration the treating solution 210 proved to be 99.9999% effective against the organisms in Table 1.

Table 2 summarizes the results of toxicology testing. Both the concentrated and use dilution formula treating solution 210 toxicology results are presented. Based on the EPA toxicity categorization of antimicrobial products that ranges from Category I (high toxicity) down to Category IV, the use dilution treating solution 210, with its combination of the biocidal properties of ionic silver and citric acid, is an EPA Category IV antimicrobial for which precautionary labeling statements are normally not required. The concentrated treating solution 210 has been placed in Category III. This compares with Category II warning statements for most leading brands of antimicrobial products. The toxicity of both the concentrated and use dilution treating solutions 210 have been assessed in extensive laboratory testing, including acute and chronic toxicity tests and dermal sensitization studies as illustrated in Table 2.

TABLE 1

TABLE 1. Testing Results - Use Dilution Treating Solution 210

|  | KILL TIME |
|---|---|
| BACTERIA | |
| Proprionibacterium acnes ATCC 6921 | 15-seconds |
| *Pseudomonas aeruginosa* ATCC 15422 | 30-seconds |
| *Staphylococcus aureus* ATCC 6538 | 30-seconds |
| *Salmonella cholerasuis* ATCC 10708 | 30-seconds |
| *Listeria monocytogenes* ATCC 19111 | 30-seconds |
| *E. coli* 0157 ATCC 43888 | 2-minute |
| *Enterococcus facium* (VRE) ATCC 700221 | 2-minute |
| *Staphylococcus aureus* (MRSA) ATCC 700698 | 2-minute |
| VIRAL | |
| HIV type1, Strain HTLV = $III_B$ | 30-second |
| Herpes simplex type I ATCC VR-733, Strain F(1) | 1-minute |
| Rhinovirus R37 ATCC VR-1147, Strain 151-1 | 10-minute |
| Influenza A ATCC VR-544, Hong Kong Strain | 10-minute |
| Poliovirus type 2 ATCC VR-1002, Strain Lansing | 10-minute |
| Fungal | |
| Trichophyton mentagrophytes ATCC 9533 | 10-minute |

TABLE 2

TABLE 2. Summary of Toxicology Results - Use Dilution Treating Solution 210

| Toxicology Condition | Concentrated Treating Solution 210 | Use Dilution Treating Solution 210 |
|---|---|---|
| Acute Dermal LD50 (rat): | >5000 mg/kg | >5000 mg/kg |
| Skin Irritation: | Slight | Non-irritating |
| Oral Toxicity: | >5000 mg/kg | >5000 mg/kg |
| Eye Irritation: | Mild, Category III | Practically non-irritating |
| Dermal Sensitization: | Not a contact sensitizer | Not a contact sensitizer |
| Carcinogenicity: | Not listed by ACGIH, IARC, NIOSH, NTP or OSHA | Not listed by ACGIH, IARC, NIOSH, NTP or OSHA |
| Epidemiology: N/A | N/A | N/A |
| Teratogenicity: N/A | N/A | N/A |
| Neurotoxicity: N/A | N/A | N/A |

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A process for treating impure water, comprising:
    forming a solution of electrolytically generated silver citrate by electrolytically generating silver ions within a solution of citric acid and water to have a concentration between 500 and 10,000 parts per million of electrolytically generated silver citrate in water; and introducing the solution of electrolytically generated silver citrate into the impure pure water.

2. A process for treating impure water, comprising:

forming a solution of electrolytically generated silver citrate by electrolytically generating silver ions within a solution of citric acid and water to have a concentration of 2000 parts per million of electrolytically generated silver citrate in water; and introducing the solution of electrolytically generated silver citrate into the impure water.

3. A process for treating impure water, comprising:

forming a solution of electrolytically generated silver citrate by electrolyticall generating silver ions within a solution of citric acid and water to have a compentration of 2000 parts per million of electrolytically generated silver citrate in water; and introducing the solution of electrolytically generated silver citrate into the impure water at a concentration of 100 parts per billion of impure water.

4. A process for treating impure water, comprising:

forming a solution of electrolytically generated silver citrate by electrolytically generating silver ions within a solution of citric acid and water to have a concentration in excess of 0.05% by volume of electrolytically generated silver citrate; and introducing the solution of electrolytically generated silver citrate into the impure water.

5. A process for treating impure water, comprising:

forming a solution of electrolytically generated silver citrate by electrolytically generating silver ions within a solution of water and approximately 5.0% to 20.0% citric acid by volume; and introducing the solution of electrolytically generated silver citrate into the impure water.

6. A process for treating impure water, comprising:

forming a solution of electrolytically generated silver citrate by electrolytically generating silver ions within a solution of water and approximately 5.0% to 20.0% citric acid by volume to produce approximately 0.0005% to 0.002% by volume of electrolytically generated silver citrate; and introducing the solution of electrolytically generated silver citrate into the impure water.

7. A process for treating impure water, comprising:

forming a solution of electrolytically generated silver citrate by electrolytically, generating silver ions within a solution of citric acid and water; and introducing the solution of electrolytically generated silver citrate into the impure water by continuously metering the solution of electrolytically generated silver citrate into moving impure water at a concentration of 100 parts per billion of impure water.

8. A process for treating impure water, comprising:

forming a solution of electrolytically generated silver citrate by electrolytically generating silver ions within a solution of citric acid and water; and introducing the solution of electrolytically generated silver citrate into moving impure water at a concentration of 100 parts per billion of impure water.

9. A process for treating impure water, comprising:

forming a solution of electrolytically generated silver citrate by electrolytically generating silver ions within a solution of citric acid and water, and introducing the solution of electrolytically generated silver citrate into a batch of the impure water at a concentration of 100 parts per billion of impure water.

10. A process for treating impure water, comprising:

forming a solution of electrolytically generated silver citrate by electrolytically generating silver ions within a solution of citric acid and water to form a treating solution of electrolytically generated silver citrate acid and water; and introducing the treating solution of electrolytically generated silver citrate into the impure water at a concentration of 100 parts per billion of impure water.

* * * * *

UNITED STATES PATENT AND TRADEMARK OFFICE
CERTIFICATE OF CORRECTION

PATENT NO. : 6,890,953 B2 Page 1 of 1
DATED : May 10, 2005
INVENTOR(S) : Andrew B. Arata It is certified that error appears in the above-identified patent and that said Letters Patent is hereby corrected as shown below:

Column 13,
Line 15, please delete "electrolyticall" and replace therefore with -- electrolytically --.
Lines 16 and 17, please delete "compentration" and replace therefore with
-- concentration --.

Column 14,
Line 9, please delete the comma (,) between "electrolytically" and "generating".

Signed and Sealed this

Ninth Day of August, 2005

JON W. DUDAS
*Director of the United States Patent and Trademark Office*